(12) United States Patent
Wagner et al.

(10) Patent No.: US 8,363,213 B2
(45) Date of Patent: Jan. 29, 2013

(54) METHOD FOR DETECTING IMPURITIES ON A SURFACE

(75) Inventors: Eva Wagner, Bad-Dürkheim (DE); Thomas Brinz, Bissingen (DE); Thomas Geiger, Walddorfhaeslach (DE); Jane Lewis, Wales (GB); Markus Tiefenbacher, Fellbach-Schmiden (DE); Tobias Burk, Tuebingen (DE); Sebastian Koltzenburg, Dannstadt (DE); Wolfgang Schrof, Neuleiningen (DE)

(73) Assignees: Robert Bosch GmbH, Stuttgart (DE); BASF AG, Ludwigshafen (DE)

( * ) Notice: Subject to any disclaimer, the term of this patent is extended or adjusted under 35 U.S.C. 154(b) by 645 days.

(21) Appl. No.: 12/444,750

(22) PCT Filed: Sep. 11, 2007

(86) PCT No.: PCT/EP2007/059526
§ 371 (c)(1),
(2), (4) Date: Feb. 25, 2010

(87) PCT Pub. No.: WO2008/052836
PCT Pub. Date: May 8, 2008

(65) Prior Publication Data
US 2010/0328676 A1    Dec. 30, 2010

(30) Foreign Application Priority Data
Oct. 31, 2006  (DE) ........................ 10 2006 051 313

(51) Int. Cl.
*G01N 21/88* (2006.01)

(52) U.S. Cl. .................................................. 356/237.3
(58) Field of Classification Search ....................... None
See application file for complete search history.

(56) References Cited

U.S. PATENT DOCUMENTS

| 5,648,047 A | 7/1997 | Kardish et al. |
| 5,844,682 A * | 12/1998 | Kiyomoto et al. ......... 356/237.1 |
| 6,449,035 B1 | 9/2002 | Batchelder |

FOREIGN PATENT DOCUMENTS

| DE | 3019341 | 11/1981 |
| EP | 0447158 | 9/1991 |
| GB | 2280133 | 1/1995 |
| WO | WO 99/39176 | 8/1999 |
| WO | WO 2006/082446 | 8/2006 |

OTHER PUBLICATIONS

International Search Report, PCT International Patent Application No. PCT/EP2007/059526, dated Dec. 11, 2007.

* cited by examiner

*Primary Examiner* — Tu Nguyen
(74) *Attorney, Agent, or Firm* — Kenyon & Kenyon LLP

(57) ABSTRACT

A method is provided for detecting not fully set coatings and liquid or smearing impurities on a surface, in which in a first step a film is pressed onto a surface of a coating using a predefined press-on pressure, the film having a relative motion with respect to the surface of the coating, thereafter the film is pulled off the surface of the coating and finally it is determined whether impurities are adhering to the film. A device is also provided for performing the method, including at least one film, which may be pressed against a surface to be tested, at least one press-on roller having a surface by which the film is pressed against the coating, and at least one device for determining whether there are impurities adhering to the film.

18 Claims, 2 Drawing Sheets

METHOD FOR DETECTING IMPURITIES ON A SURFACE

FIELD OF THE INVENTION

The present invention relates to a method for detecting not fully set coatings and liquid or smearing impurities on a surface. The present invention furthermore relates to a device for performing the method.

BACKGROUND INFORMATION

Measuring instruments are often mounted in a contacting manner for testing chemical, mechanical, and optical properties of surfaces, for example, of lacquers. These include, for example, color and brightness measuring instruments, layer thickness measuring instruments, and hardness measuring instruments.

If a coating is applied to a substrate which is not fully set, the measuring head may contact the coating when mounting the measuring instrument. This causes the measuring head to become contaminated; further measurements may be distorted and the contamination may be entrained onto subsequent substrates. The measuring instrument may even become irreparably damaged. If the measuring head has contacted a not fully set coating, the measuring head must be cleaned. Reasons for not fully set coatings may include, for example, unoptimized formulations, incorrect hardening conditions, or interference in the hardening systems.

Furthermore, it is also possible that surfaces become glued together or contaminated during handling and storage of the objects. Contaminations may also occur due to handling systems or storage systems such as shelves or racks and the like.

Common damage patterns of insufficiently set coatings include, for example, liquid coating material, soft or smearing surfaces, or a solid, hardened film over soft or liquid coating material. The coating material, the surface, or the solid, hardened film may or may not be adhesive.

To test the drying state of a lacquer, generally simple, manual methods are used in the lab. For example, glass beads are spread onto the surface or, pursuant to DIN 53150, paper having a defined weight is pressed onto the surface. It is tested whether it is possible to remove the beads or the paper without damaging the coating or using excessive force. The damage to the coating is verified by a visual check.

In another method generally used in the lab, the surface of the coating is scratched using a fingernail, and the possibly occurring damage pattern is evaluated, for example, using scrapers or via color transfer onto the finger or by detaching a film from the coating. A solid film over liquid or soft, not fully set material may thus also be detected. This is important in particular in the case of lacquers which are set in the presence of UV radiation.

The disadvantage of the above tests is, however, that they are not easily automated; in addition, they are inaccurate and depend on the tester. In many cases, only a rough estimation of "OK" or "not OK" is carried out.

SUMMARY

A method according to an example embodiment of the present invention for detecting not fully set coatings and liquid or smearing impurities on a surface includes the following steps:
(a) pressing a film onto the surface using a predefined press-on pressure, the film having a relative motion with respect to the surface,
(b) pulling the film off the surface,
(c) determining whether impurities are adhering to the film.

Impurities on the surface or also material of the coating when the coating has not fully set are transferred to the film by pressing the film onto the surface. If a film has formed on a not fully set coating, the film is pulled to the side and torn off using the relative motion of the film induced under pressure. The liquid or soft coating material underneath the film, which has not yet set, may pour out and is transferred to the film. By determining whether impurities are adhering to the film, it may be detected whether lacquer has been transferred to the film due to the film being pressed onto the coating. To determine whether impurities are adhering to the film, the film may be transluminated using a light source, for example. The light passing through the film may be detected, for example, by using a photodetector. If material has been transferred to the film, the intensity of the passing light is modified. Alternatively, ultrasonic methods or other optical methods, for example, camera systems, may also be used to determine whether impurities are adhering to the film.

The advantage of the method according to the present invention is that it is independent of an evaluation by a tester. In addition, the method may be automated if a new, clean piece of film is used for each new coating sample.

In a preferred specific embodiment, the film is pulled off a film reserve and, after the determination in step (c), it is collected for disposal. By pulling the film off a film reserve, a new, clean piece of film is available for each coating to be tested. The method may thus be automated. A reel, for example, onto which the film is wound, is suitable as a film reserve. The film is collected for disposal preferably by winding the film onto a reel. The film is preferably transported by driving the reel onto which the film is wound using a motor.

Furthermore, however, it is also possible that the film is an endless film, which runs around at least two reels, one of which is driven, the film being cleaned after being transluminated in step (c) and before being pressed again onto the surface of the coating. The advantage of using an endless film is that no contaminated film needs to be disposed of. It is, however, preferable to use a film which, after the determination in step (c), is collected for disposal, since when cleaning procedures are used, residues may remain on the film, cleaning may not be possible, or the film may be damaged.

The coating which is tested using the method according to the present invention may be a paint or a colored lacquer. It is also possible that the coating is a clear lacquer. This means that the method is suitable either for covering, pigmented, or also for transparent substances which may or may not contain coloring agents. Whether or not the coating is colored is irrelevant for performing the method.

If the coating is a paint or a colored lacquer, the film is clear and transparent in one specific embodiment. If impurities or unset coating material are transferred to the film, its transparency is diminished if, for example, the light is scattered or absorbed by pigments and thus weakened. If the determination of whether there are impurities on the film is made by transluminating the film and detecting the passing light, this results in a reduction in the light intensity detected by the photodetector.

Alternatively, an opaque and/or light-scattering film may also be used. For example, the film is coated using a matte clear lacquer for this purpose. Also, if an opaque and/or light-scattering film is wetted by impurities or coating material after the film is pressed onto the surface, the intensity of the passing light is reduced.

If the coating is a clear lacquer, an opaque and/or light-scattering film is preferably used. When the opaque and/or light-scattering film is wetted by a clear liquid, such as, for example, the unset clear lacquer, the intensity of the passing light increases, since the scattering of the light by the matte surface of the film diminishes because it is coated by the clear liquid. This may also be detected by using the photodetector.

To perform the example method according to the present invention in an automated manner, in a preferred specific embodiment a surface is labeled "not OK" if the transmission of light through the film changes at least by a predefined amount. To prevent production-related transmission differences from causing surfaces that are "OK" to be labeled "not OK," the predefined amount of change in the transmission is, for example, at least 5%. Production-related transmission changes in the film may occur, for example, due to fluctuations in the film thickness. The sensor may preferably be calibrated to the film being used.

The present invention furthermore relates to a device for performing the method according to the present invention, the device including at least one film, which may be pressed against a surface, at least one press-on roller having a surface by which the film is pressed against the surface to be tested, and at least one device for determining whether the film has impurities. In one specific embodiment, the device includes at least one light source and at least one photodetector for determining whether the film has impurities, the light source and the photodetector being situated in such a way that the film is passed between the light source and the photodetector after it is pulled off the surface to be tested.

In one specific embodiment, the surface of the press-on roller is smooth or profiled. The press-on roller is preferably profiled. Due to the profile, a structured transfer is possible, whereby the detection of substances difficult to detect is facilitated. Also, by using a profiled press-on roller, a stable film which has formed on a not yet set, liquid or soft coating material is more easily torn open.

The material of the press-on roller may be hard or soft to achieve a larger or smaller press-on surface area. A hard material results in a smaller press-on surface area, and a soft material results in a larger press-on surface area. For highly adhesive surfaces, a small press-on surface area is preferred, while for very free-flowing surfaces a large press-on surface area is preferred to enhance the transfer onto the film and to limit the adhesive force.

To perform the example method in an automated manner, the film is preferably kept wound on a reel from which it may be unwound. The device preferably also includes a reel onto which the film is wound after being transluminated.

Alternatively, it is also possible that the film is an endless film, which runs around at least the press-on roller and another reel. If an endless film is used, it is preferable that the device also includes a cleaning device, in which the film may be cleaned and, if necessary, dried after translumination. By cleaning the film after translumination, transferred impurities or coating residues are not transferred to a new sample or evaluated as impurities of another sample.

Furthermore, the example device includes, in a preferred specific embodiment, an analyzer unit, which is connected to the device for determining whether the impurities are adhering to the film, in order to be able to perform an automated analysis.

BRIEF DESCRIPTION OF THE DRAWINGS

Exemplary embodiments of the present invention are illustrated in the drawings and explained in greater detail in the description that follows.

DETAILED DESCRIPTION OF EXAMPLE EMBODIMENTS

Figure 1:
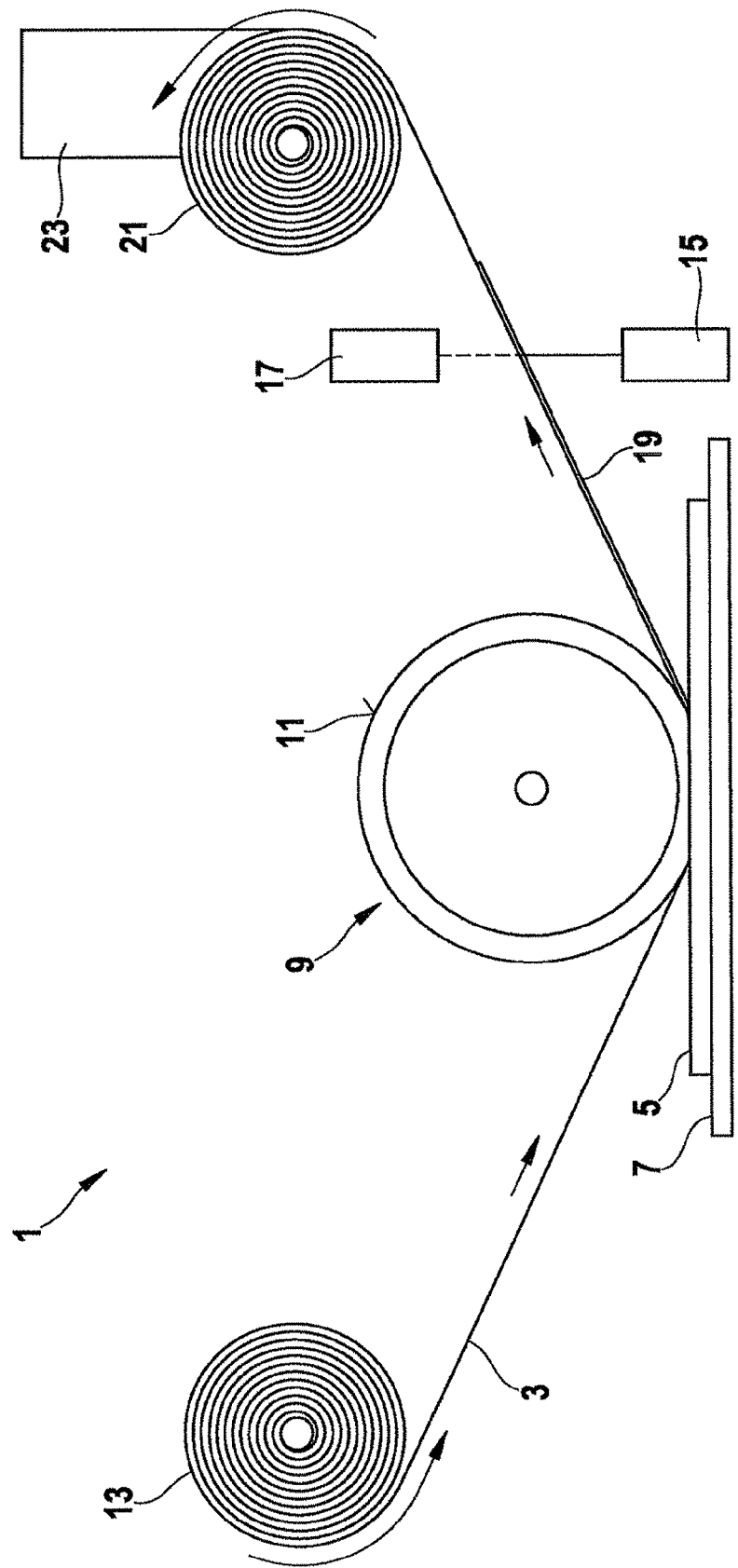
FIG. 1 shows the structure of an example measuring device designed according to the present invention.

FIG. 1 shows the structure of an example measuring device designed according to the present invention.

A measuring device 1 designed according to the present invention includes a film 3, which is pressed against a surface to be tested of a substrate 7. The surface to be tested may be, for example, a coating 5 of a paint, a colored lacquer, or a clear lacquer. Furthermore, an uncoated surface to be tested may also be tested using measuring device 1 designed according to the present invention. Metals, plastics, glass, wood, etc., may be used, for example, as material for the substrate. The material of the substrate depends on the application for which the coating material is to be used. Film 3 is pressed on the surface to be tested with the help of a press-on roller 9. Press-on roller 9 is provided with a surface 11 which may have a smooth or profiled design. Surface 11 of press-on roller 9 preferably has a profiled design.

Film 3 is preferably kept wound on a reel 13. By unwinding film 3 from reel 13, it is ensured that a new piece of film 3 is used for each surface to be tested. By using a new piece of film 3 every time, no cleaning effort is needed and a faster, automated sample change, which is safer for the process, is possible. Substrate 7 having coating 5 formed thereon is considered a "sample" as defined for the purposes of the present invention. After film 3 has been pressed onto the surface, it is transluminated by a light source 15. The light emitted by light source 15 and passing through the film is received by a photodetector 17. If the surface to be tested is a coating 5, which has not yet fully set, a dry film has been formed on the not yet fully set coating 5, or the surface to be tested is contaminated, coating material or part of the impurities is transferred from the surface to be tested to film 3. A film 19 is thus formed on film 3. The light emitted by light source 15 and passing through film 3 is dampened by film 19. The light intensity received by photodetector 17 is thus weaker when a film 19 is present on film 3. This allows the recognition of whether coating 5 has not fully set or is contaminated. Instead of light source 15 and photodetector 17, any other device using which it may be ascertained whether impurities have been transferred from the surface to be tested to film 3 may also be used. Suitable measuring devices include, for example, optical systems in which impurities are detected by a camera or also ultrasonic methods.

After it is determined whether there are impurities on film 3, film 3 is wound onto a second reel 21. Second reel 21 my be driven, for example, by a motor 23.

To test whether coating 5 has not fully set or whether there are liquid or smearing impurities on coating 5 or on the uncoated surface to be tested, substrate 7 having the surface to be tested is positioned underneath press-on roller 9. Film 3 is pressed onto the surface to be tested with the help of a press-on roller 9. A piece of film 3 is wound onto second reel 21 with the aid of motor 23. Film 3 is drawn over the surface to be tested, whereby film 3 has a relative motion with respect to the surface to be tested. The relative velocity between the surface to be tested and film 3 may be achieved, for example, by clamping substrate 7 having the surface to be tested, while film 3 is moved; furthermore, it is possible that the substrate having the surface to be tested and film 3 are moved at different velocities, or that substrate 7 having the surface to be tested is drawn through underneath film 3, while film 3 remains stationary. However, preferably substrate 7 having the surface to be tested is clamped and film 3 is moved over the surface to be tested. If a coating 5, which is applied to the surface to be tested has not yet fully set, if a dry film has been formed on the not yet fully set coating 5 and the coating material underneath the film is still liquid or soft, or if the surface to be tested is contaminated, a part of the impurities or of the liquid or soft coating material adheres to film 3 as film 19. After pulling film 3 off the surface to be tested, film 3 possibly having film 19 adhering thereto may be transluminated by light source 15. The light passing through film 3 and possibly through film 19 is received by photodetector 17. The transmission value for a film 3 to which no film 19 adheres is used as a reference value. If a film 19 adheres to film 3, the value received by the photodetector changes. This allows one to recognize whether or not coating 5 is "OK". As explained previously, instead of light source 15 and photodetector 17, any other suitable measuring device may be used for detecting whether there are impurities on film 3.

After the surface has been tested, substrate 7 having the surface to be tested is removed, and it is possible to place a next substrate 7 having another surface to be tested under press-on roller 9. If photodetector 17 is connected to an analyzer unit, the surface testing method may be automated.

Not fully set coatings 5 or contaminated surfaces may be sorted out fully automatically using the method according to the present invention. Another advantage is that only a small measuring spot is produced on coating 5 and samples that are "OK" are not damaged. For this reason, tested samples, when they are "OK," may be further used without limitations.

Figure 2:
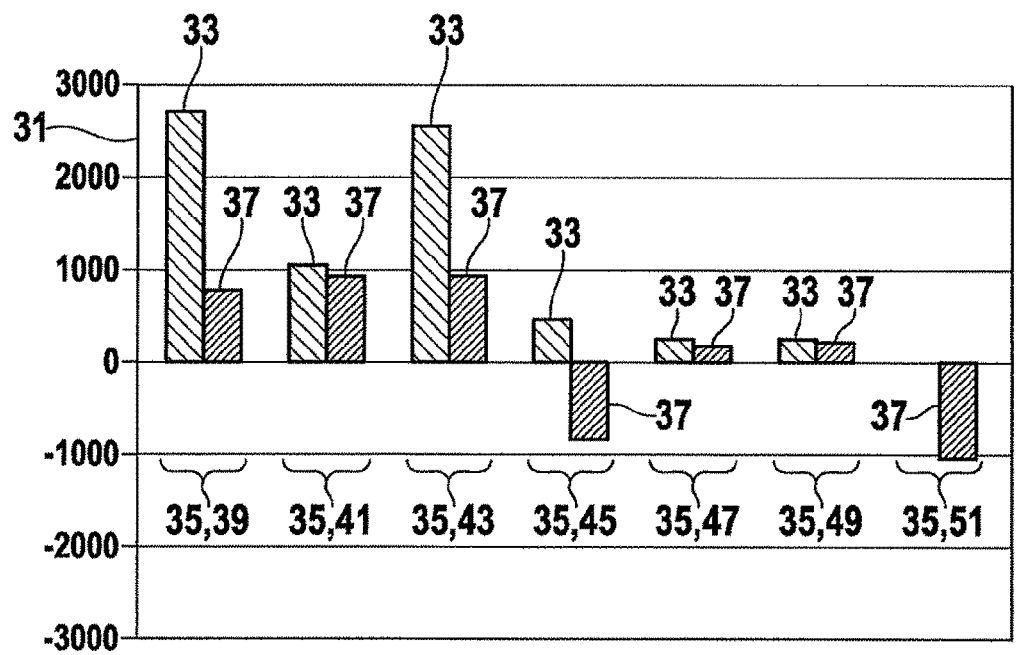
FIG. 2 shows a difference between the measured values of a clean and a contaminated film in a bar diagram.

FIG. 2 shows a difference between the measured values of a clean and a contaminated film in a bar diagram. The difference is plotted on y axis 31. FIG. 2 shows a clear, transparent film and an opaque film for comparison.

In FIG. 2 a first pair of bars 39 shows the difference of the measured values between a clean and a contaminated film for a clear, transparent film in the left-hand bar 33 and an opaque film in the right-hand bar 37 for a UV-setting yellow lacquer, which is transferred to the film in liquid form. Film 19, which forms on film 3, is colored. The difference between the measured values of a clean and a contaminated film for a UV-setting yellow lacquer in which a film has been formed underneath which there is an unset, liquid or soft lacquer is plotted in the second pair of bars 41. In FIG. 2, a third pair of bars 43 shows the difference between the measured values of a clean and a contaminated film for a yellow UV-setting lacquer having a film, the film having been mechanically torn. The lacquer under the film, which has not yet set, is transferred to film 3 as colored film 19. Fourth pair of bars 45 shows the difference in the measured values of a clean and a contaminated film for a burnt-in clear lacquer, which has become touch-dry. The touch-dry burnt-in clear lacquer is still sticky. There is a clear, structured transfer to the film. It is apparent that the transmission of light decreases in the case of a clear, transparent film, whereas the transmission increases in the case of an opaque film.

Fifth pair of bars 47 shows the difference in the measured values between a clean and a contaminated film for a UV-setting clear lacquer, which is also still sticky, a cloudy film 19 being formed on film 3. Sixth pair of bars 49 shows the difference for a second UV-setting clear lacquer. In seventh pair of bars 51, the difference for a liquid, UV-setting clear lacquer is shown, a clear film 19 being formed. Due to the clear film 19, the transparency of film 3 to light does not change when a clear, transparent film is used. In the case of an opaque film, the transparency to light is improved.

FIG. 2 shows that both for clear, transparent films and for an opaque film, in the case of colored lacquers, the light intensity recorded by photodetector 17 decreases in the case of a colored film 19 formed on film 3. The decrease in intensity is considerably greater than the decrease in intensity in the case of a cloudy film 19, which is obtained in the case of a not yet completely set clear lacquer on film 3. If a clear film is formed on film 3 when studying a clear lacquer, the light intensity ascertained by photodetector 17 increases. A liquid film of a clear lacquer cannot be ascertained using a clear, transparent film, as is apparent in seventh pair of bars 51. For this reason, an opaque film should be used for testing clear lacquers.

Figure 3:
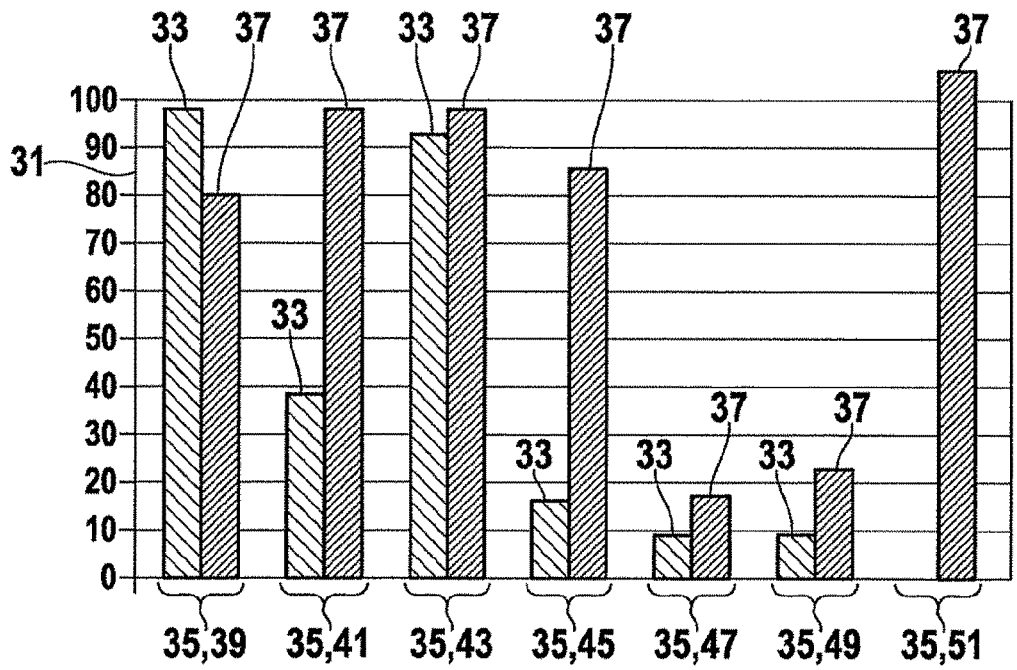
FIG. 3 shows a change in the transmission in coatings having different degrees of setting in a bar diagram.

FIG. 3 shows the change in transmission in a bar diagram.

Unlike FIG. 2, FIG. 3 shows the change in transmission in % plotted on y axis 31. The samples for which the seven pairs of bars 39, 41, 43, 45, 47, 49 and 51 represent the change in transmission are the same as in FIG. 2. From FIG. 3 it is apparent that, except for the liquid, UV-setting clear lacquer, the change in transmission is at least 9%, even when using a clear, transparent film. Only in the case of the liquid, UV-setting clear lacquer does the transmission not change for the clear, transparent film. When using an opaque film, right-hand bars 37 make it apparent that the change in transmission is greater than 15% in each case. Even in the case of a liquid, UV-setting clear lacquer, which is transferred to film 3 as liquid film 19, seventh pair of bars 51 shows a noticeable change in the transmission. For this reason, the use of an opaque film is preferred for the example method according to the present invention.

What is claimed is:

1. A method for detecting not fully set coatings and liquid or smearing impurities on a surface to be tested, comprising:
   pressing a film onto the surface to be tested using a predefined press-on pressure, the film having a relative motion with respect to the surface to be tested;
   pulling the film off the surface to be tested; and
   determining, by a determining device, whether impurities are adhering to the film prior to the film being wound unto a reel.

2. The method as recited in claim 1, wherein the film is pulled off a film reserve and, after the determination of whether impurities are adhering to the film, the film is collected for disposal.

3. The method as recited in claim 1, wherein the film is an endless film, which runs around at least two reels, at least one of which is driven, the film being cleaned after the determining step has been performed and before being pressed again onto a surface to be tested.

4. The method as recited in claim 1, wherein the coating is a paint or a colored lacquer.

5. The method as recited in claim 4, wherein the film is clear and transparent.

6. The method as recited in claim 1, wherein the coating is a clear lacquer.

7. The method as recited in claim 6, wherein the film is at least one of opaque and light-scattering.

8. The method as recited in claim 1, wherein, for determining whether impurities are adhering to the film, the film is transluminated using a light source and light passing through the film is detected by a photodetector.

9. The method as recited in claim 8 wherein a surface to be tested is labeled "not OK" if the transmission of light through the film changes by at least a predefined amount.

10. The method as recited in claim 8, wherein the light source and the photodetector are situated in such a way that the film is passed between the light source and the photodetector after it is pulled off the surface to be tested.

11. A device for detecting not fully set coatings and liquid or smearing impurities on a surface to be tested, comprising:
- at least one film which may be pressed against a surface to be tested;
- at least one press-on roller having a surface by which the film is pressed against the coating; and
- at least one device for determining whether there are impurities adhering to the film prior to the film being wound unto a reel.

12. The device as recited in claim 11, wherein the device for determining whether impurities are adhering to the film includes at least one light source and at least one photodetector, the light source and the photodetector being situated in such a way that the film is passed between the light source and the photodetector after it has been pulled off the coating.

13. The device as recited in claim 11, wherein the surface of the press-on roller is smooth or profiled.

14. The device as recited in claim 11, wherein the film is kept on a reel from which it may be unwound.

15. The device as recited in claim 11, further comprising: a second reel onto which the film is wound after being transluminated.

16. The device as recited in claim 15, further comprising: an analyzer unit which is connected to the photodetector to perform an automatic analysis.

17. The device as recited in claim 11, wherein the film is an endless film, which runs around at least the press-on roller and another reel.

18. The device as recited in claim 17, further comprising: a cleaning device in which the film may be cleaned after being transluminated.

* * * * *

UNITED STATES PATENT AND TRADEMARK OFFICE
CERTIFICATE OF CORRECTION

PATENT NO.        : 8,363,213 B2                         Page 1 of 1
APPLICATION NO. : 12/444750
DATED             : January 29, 2013
INVENTOR(S)       : Wagner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 945 days.

Signed and Sealed this

First Day of September, 2015

Michelle K. Lee
*Director of the United States Patent and Trademark Office*